(12) United States Patent
Gemmiti et al.

(10) Patent No.: US 7,416,884 B2
(45) Date of Patent: Aug. 26, 2008

(54) BIOREACTOR AND METHODS FOR TISSUE GROWTH AND CONDITIONING

(75) Inventors: Christopher Vinson Gemmiti, Jonesboro, GA (US); Robert E. Guldberg, Marietta, GA (US)

(73) Assignee: Georgia Tech Research Corporation, Atlanta, GA (US)

( * ) Notice: Subject to any disclaimer, the term of this patent is extended or adjusted under 35 U.S.C. 154(b) by 234 days.

(21) Appl. No.: 10/788,135

(22) Filed: Feb. 26, 2004

(65) Prior Publication Data

US 2005/0009179 A1    Jan. 13, 2005

Related U.S. Application Data

(60) Provisional application No. 60/450,443, filed on Feb. 26, 2003.

(51) Int. Cl.
*C12M 3/00* (2006.01)
*C12M 3/06* (2006.01)

(52) U.S. Cl. .................. 435/293.1; 435/297.2; 623/915; 210/321.84

(58) Field of Classification Search ............. 435/293.1, 435/297.2; 623/915; 210/321.84
See application file for complete search history.

(56) References Cited

U.S. PATENT DOCUMENTS

| | | | | |
|---|---|---|---|---|
| 2,712,386 A | * | 7/1955 | Jones et al. | 210/775 |
| 4,367,146 A | | 1/1983 | Pollock | |
| 4,681,853 A | * | 7/1987 | Hardy et al. | 435/287.2 |
| 4,762,794 A | * | 8/1988 | Nees | 435/297.2 |
| 5,153,131 A | | 10/1992 | Wolf | |
| 5,190,878 A | * | 3/1993 | Wilhelm | 435/297.2 |
| 5,459,069 A | | 10/1995 | Palsson | |
| 5,645,726 A | | 7/1997 | Pollack | |
| 5,843,766 A | * | 12/1998 | Applegate et al. | 435/284.1 |
| 5,928,945 A | | 7/1999 | Seliktar et al. | |
| 5,989,913 A | | 11/1999 | Anderson | |
| 6,121,042 A | | 9/2000 | Peterson et al. | |
| 6,140,039 A | | 10/2000 | Naughton et al. | |
| 6,242,247 B1 | | 6/2001 | Riesser et al. | |
| 2003/0157709 A1 | | 8/2003 | DiMilla et al. | |

OTHER PUBLICATIONS

Adkisson et al., Clin. Orthop., 139S: S280-S294 (2001).
Guilak et al., Clin. Orthop., 391S: S295-S305 (2002).
Jockenhoevel, S. et al., Cardiovascular Tissue Engineering: A New Laminar Flow Chamber for In Vitro Improvement of Mechanical Tissue Properties ASAIO Journal, 48(1): 8-11 (2002).
Levesque, M.J. and R.M. Nerem, The elongation and orientation of cultured endothelial cells in response to shear stress. J Biomech Eng., 107(4):341-7 (1985).
Malaviya, P., et al., Fluid-induced shear stresses promote chondrocyte phenotypic alteration. Transactions of the Orthopaedic Research Society, 44th Annual Meeting: p. 228 (1998).

(Continued)

*Primary Examiner*—William H Beisner
(74) *Attorney, Agent, or Firm*—Law Office of Collen A. Beard, LLC

(57) ABSTRACT

A bioreactor and methods of using same for making tissue constructs and for conditioning tissue-engineered constructs and harvested tissues such as cryopreserved tissues. The bioreactor allows for static and dynamic culture/conditioning. The bioreactor is dual chambered (one chamber above and one below the cells or construct) to allow for application of biochemical and/or biomechanical stimuli to each side of the cells/construct.

4 Claims, 2 Drawing Sheets

OTHER PUBLICATIONS

Masuda et al., J Ortho Res, 21:139-148 (2003).

Mauck RL, Soltz MA, Wang CC, Wong DD, Chao PH, Valhmu WB, Hung CT, Ateshian GA, Functional tissue engineering of articular cartilage through dynamic loading of chondrocyte-seeded agarose gels, J Biomech Eng. 122(3):252-60 (Jun. 2002).

Mauck RL, Seyhan SL, Ateshian GA, Hung CT., Influence of seeding density and dynamic deformational loading on the developing structure/function relationships of chondrocyte-seeded agarose hydrogels., Ann Biomed Eng. 30(8):1046-56 (Sep. 2002).

Malaviya, P. and Nerem, R.M, Steady shear stress stimulates bovine chondrocyte proliferation in monolayer cultures. Transactions of the Orthopaedic Research Society, 45th Annual Meeting: p. 8. (1999).

Nackman, G., et al. Surgery 124(2):353-361 (Aug. 1998).

Pazzano D, Mercier KA, Moran JM, Fong SS, DiBiasio DD, Rulfs JX, Kohles SS, Bonassar LJ, Comparison of chondrogensis in static and perfused bioreactor culture, Biotechnol Prog. 16(5):893-6 (Sep. 2000).

Riesle, J. et al., Collagen in Tissue-Engineered Cartilage: Types, Structure, and Crosslinks, J. Cell. Biochem. 71:313-327 (1998).

Smith, R., et al., Effects of shear stress on articular cartilage metabolism. Biorheology, 37:95-107 (2000).

Smith, R.L., et al., Effects of fluid-induced shear on articular chondrocyte morphology and metabolism in vitro. J Orthop Res, 13(6):824-31 (1995).

Vunjak-Novakovic G, Martin I, Obradovic B, Treppo S, Grodzinsky AJ, Langer R, Freed LE, Bioreactor cultivation conditions modulate the composition and mechanical properties of tissue-engineered cartilage, J Orthop Res. 17(1):130-8 (Jan. 1999).

Waldman, S.D. et al., J. Bone & Joint Surgery 85A (Supp. 2): 101-105 (2003).

Wang, T. et al., Experimental Hematology 23:26-32 (1995).

Williams KA, Saini S, Wick TM., Computational fluid dynamics modeling of steady-state momentum and mass transport in a bioreactor for cartilage tissue engineering., Biotechnol Prog. 18(5):951-63 (Sep. 2002).

Yu et al., Biomaterials, 18:1425-1431 (1997).

* cited by examiner

BIOREACTOR AND METHODS FOR TISSUE GROWTH AND CONDITIONING

CROSS-REFERENCE TO RELATED APPLICATION

This application claims priority to U.S. Provisional Application Ser. No. 60/450,443, filed on Feb. 26, 2003.

STATEMENT REGARDING FEDERALLY SPONSORED RESEARCH

This invention was made with government support under grant number EEC-9731643 awarded by National Science Foundation. The Government has certain rights in the invention.

BACKGROUND OF THE INVENTION

The invention is generally in the field of tissue engineering, more specifically in the field of growth and conditioning of tissue constructs. With the American public aging and sports-related injuries increasing, the demand for orthopedic surgeries has grown tremendously. In 1998, there were over 3 million people afflicted with such problems in the United States alone, representing both a significant clinical problem and commercial opportunity. Currently, a great deal of research is being devoted to restoring function in damaged orthopedic tissues. Restoration of function to damaged orthopedic tissues has taken many forms: autografts, allografts, xenografts, implantable (permanent and biodegradable) biomaterials, and tissue-engineered constructs. Each of these treatments has achieved some degree of success, but each has its limitations.

Two of the more attractive solutions which have recently emerged are allografts and tissue-engineered constructs. An allograft is a tissue transplanted between individuals of the same species. Allografts relieve some of the burden of a supply source, while tissue-engineered constructs can in theory be a complete off-the-shelf solution. Tissue engineering of cartilage constructs grown in vitro has emerged as a potentially more suitable treatment than allografts. However, either of these solutions will prove to be commercially viable only if the construct or allograft can restore function. Restoration of function is more likely if the implanted tissue possesses: 1) an active cellular component to facilitate remodeling, 2) similar biomechanical properties to sustain load-bearing movements, and 3) an ability to properly integrate into the host tissue for a sustained, long-term maintenance of function.

The orthopedic tissues in the body receive biomechanical stimulation; in particular, long bones, articular cartilage, and the meniscus are constantly being loaded. Prior to implantation in the body, ex vivo cultured tissues often lack the proper mechanical properties or cellular function to become fully integrated and functional. One approach to improving this deficiency is to subject the tissue to similar biomechanical loads as seen in situ, such as shear stress, prior to implantation. Reduced cellular function may also be addressed through exposure to biochemical stimuli such as growth factors. A combination of biochemical and biomechanical stimuli may be most desirable.

Integration of a construct may be better if it is heterogeneous; that is, the type of cells or characteristics of the cells varies across the construct. For example, a construct could have cartilage-like tissue on one side and bone-like tissue on the other side. Mimicking the native tissue heterogeneity in this way may accelerate the repair of defects involving tissue interfaces such as osteochondral defects.

Functional tissue engineering of cartilage involves the use of bioreactors designed to provide a controlled in vitro environment that embodies some of the biochemical and biomechanical stimuli known to regulate chondrogenesis. Various types of bioreactors have been investigated for use in producing tissue-engineered human cartilage, including rotating-wall vessels, spinner flasks, perfusion, and compression/perfusion bioreactors. In each type of reactor the flow of the culture medium causes the growing tissue to experience a different dynamic environment, potentially influencing the character of the final tissue. Three main types of forces are currently used in cartilage-culturing processes: hydrostatic pressure, direct compression, and shear fluid environments.

Prior art bioreactors provide the cells or construct with a single culturing or conditioning environment. It would be advantageous to have a bioreactor wherein biochemical and biomechanical stimuli can be applied to each side of a construct. Such a bioreactor, where the biochemical and biomechanical stimuli are different on each side, could result in a heterogeneous construct. Thicker constructs could result with the use of the same stimuli applied to both sides of the construct.

SUMMARY OF THE INVENTION

The Invention is a bioreactor (and methods of using same) for making tissue constructs and for conditioning tissue-engineered constructs and harvested tissues such as cryopreserved tissues. The bioreactor is dual chambered (one chamber above and one below the cells or construct) to allow for application of biochemical and/or biomechanical stimuli to both sides of the cells or construct. Different stimuli can be applied to each side, desirably resulting in a heterogeneous construct. The bioreactor allows for static and dynamic culture/conditioning.

The bioreactor can be used for growth of cells into a tissue construct. The bioreactor can also be used for the biochemical and/or biomechanical conditioning of tissue-engineered constructs or harvested tissues, such as cryopreserved tissue (both referred to herein as "constructs" or "tissue"), prior to implantation.

DETAILED DESCRIPTION OF THE INVENTION

As used herein, the term "construct" refers to tissue formed in a bioreactor, generally by cells proliferating and secreting extracellular matrix, tissue formed ex vivo by other means, or harvested tissue.

The term "substrate" refers to a two dimensional membrane or three dimensional scaffold to which cells can attach.

The invention is a bioreactor and methods for using the bioreactor for growth of cells on a substrate or for conditioning of tissue constructs. The bioreactor has a dual chamber design and means for applying biomechanical stimuli to the cells or construct. The dual chamber design allows for exposure of both sides of the cells or construct to biochemical and biomechanical stimuli. The bioreactor also allows for exposure of each side of the substrate or construct to different biochemical or biomechanical stimuli. The dual chamber design thus allows for feeding of cells above and below a membrane, for example, which increases the overall mass transport to the cells or construct because the available surface area is larger. As another example, the dual chamber design allows for application of shear stress to the top of a construct while the bottom of the construct is exposed to a growth factor.

The dual chamber design allows for introduction of heterogeneity in the tissue. Different cell types can be seeded and grown in the two chambers. Or cells of the same type can be exposed to different media, i.e. different growth factors or different amounts of a growth factor. A gradient of cellular phenotype should aid in integration of the construct into an implantation site. Examples are a cartilage-to-bone or periosteum-to-bone construct for implantation into a site comprising both cartilage and bone, or periosteum and bone.

The bioreactor allows for the application of both biochemical and biomechanical stimuli. In a preferred embodiment illustrated in the Figures, biochemical stimuli, in the form of growth factors, can be applied to the top and bottom faces on the construct. Biomechanical stimuli, in the form of shear stress, can be applied to the top face in laminar flow in the parallel-plate flow chamber.

The bioreactor can be used for growth of cells into a tissue construct. The bioreactor can also be used for the biochemical and/or biomechanical conditioning of both tissue-engineered constructs and harvested tissues, such as cryopreserved tissue.

I. The Device

Figure 1:
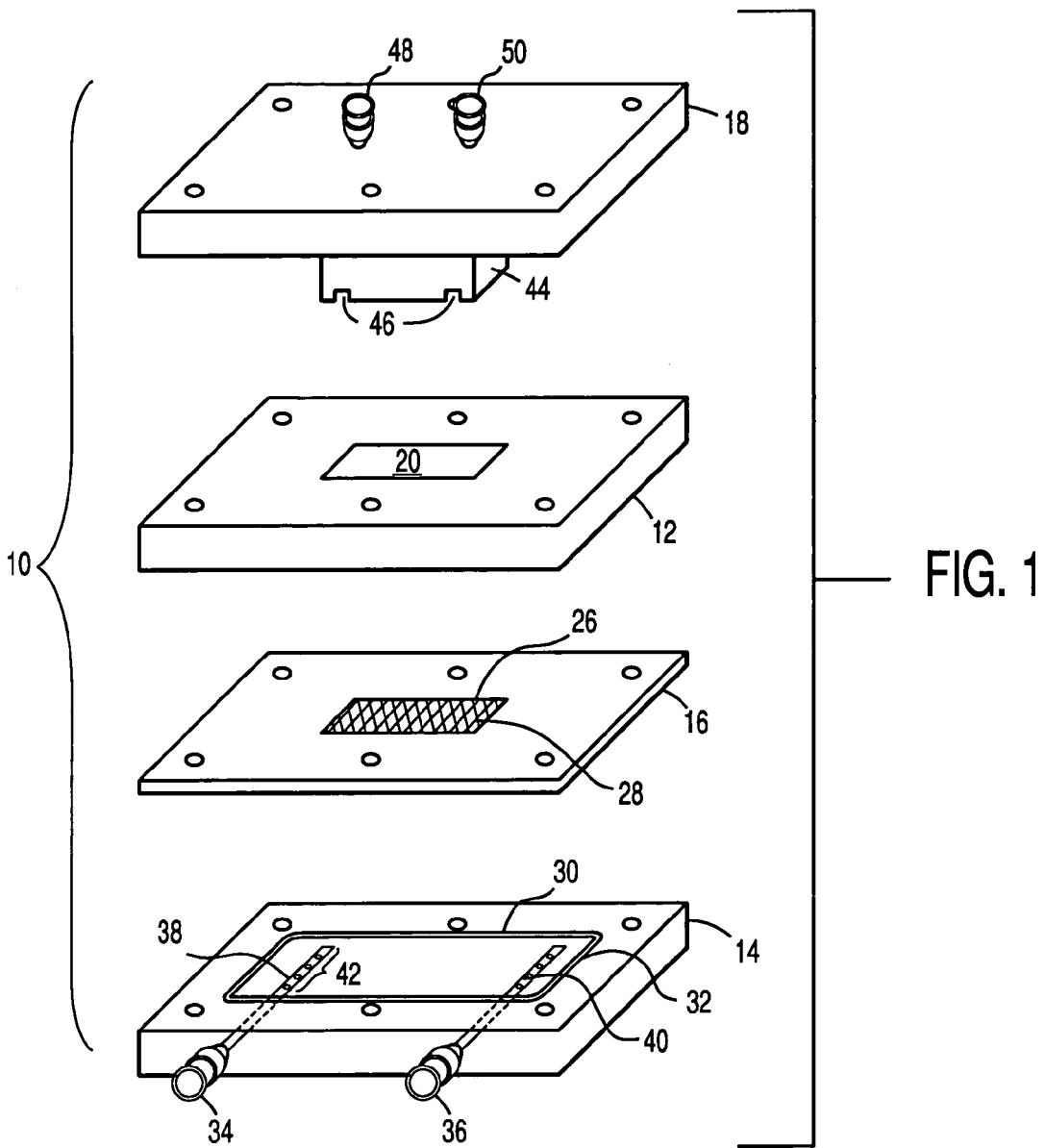
FIG. 1 is an exploded perspective view of one embodiment of the bioreactor in the "perfusion" configuration, having a cap, top plate, frame, and bottom plate.

The bioreactor 10 is shown in FIG. 1 in the configuration used for dynamic growth or conditioning, also referred to as the perfusion mode. The bioreactor includes a top plate 12 and a bottom plate 14, having frame 16 there between. The bioreactor further includes cap 18.

Figure 2:
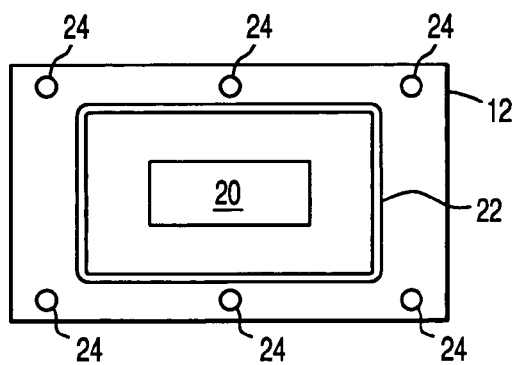
FIG. 2 is a schematic of the bottom surface of the top plate.

The bottom surface of top plate 12 is shown in FIG. 2. Top plate 12 has a cut-out region 20 which extends through the plate. Surrounding the cut out region is a gasket 22. Top plate 12 further includes a plurality of fastening holes 24 which may be threaded. As shown in FIG. 1, cap 18, frame 16, and bottom plate 14 also have a plurality of holes 24. A fastening screw, for example, (not shown) can be inserted through the holes of each part to hold the device together.

As illustrated in FIG. 1, frame 16 contains a cut-out region 26 desirably the same size as the cut out region 20 of the top plate. A membrane 28 is attached to the side of frame 16 facing the top plate 12 and covers the cut out region 26. The membrane can be attached to the frame by a variety of means.

As discussed further below, the bioreactor can be used in dynamic mode to condition the construct that has been formed in the bioreactor. If the bioreactor is used to condition a construct that has not been formed within the bioreactor, such as a cryopreserved tissue, the construct may be attached to a frame not having a membrane attached thereto. Alternatively, the construct may be placed on top of or secured to the membrane. Desirably, the placement of the construct maintains the separateness of the chambers.

Bottom plate 14 is shown in FIG. 1. The plate includes an indented region 30 into which a bottom plate gasket 32 fits. Bottom plate has two ports—an inlet 34 and outlet 36—which provide access to an inlet tube 38 and outlet tube 40, respectively. These inlet and outlet tubes each have a plurality of diffusion ports 42 along their length in the region of the tube which extends into the region of the bottom plate within the gasket 32.

Figure 3:
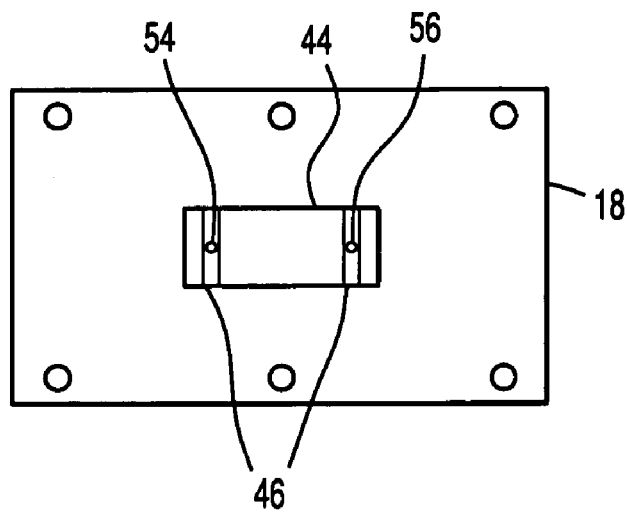
FIG. 3 is a schematic of the bottom surface of the cap.

Cap 18 is illustrated in FIG. 1 and in more detail in FIG. 3, which is a view of the bottom surface of cap 18. Cap 18 has a protrusion 44 extending from its bottom surface, having a surface area slightly smaller than that of the top plate cut out region 20. The protrusion 44 has two lateral diffusion grooves 46 on its bottom surface. Cap 18 has an inlet port 48 and an outlet port 50, and a tube 54 or 56 that passes through the cap 18 and connects the port to a diffusion groove 46.

Figure 4:
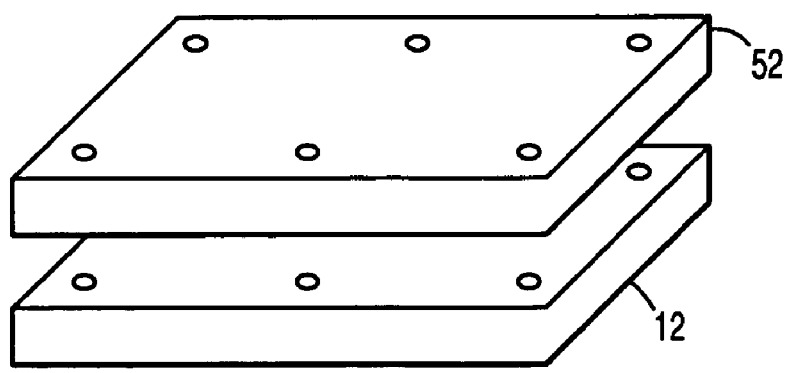
FIG. 4 is an exploded perspective view of the cover and top plate.

FIG. 4 illustrates cover 52, which fits over top plate 12 for the use of the bioreactor in static mode, as explained below.

Each of cap 18, cover 52, top plate 12, frame 16, and bottom plate 14 can be made of a variety of materials. It is important that the material not interfere with cell growth or construct conditioning. Exemplary materials are metals such as stainless steel and aluminum (with anodization), and plastics such as Plexiglas, polystyrene, polycarbonate, and polytetrafluoroethylene (PTFE). In a preferred embodiment, the cap, cover, and top and bottom plates are made from clear polycarbonate and the frame is stainless steel. The gaskets can be made from silicone rubber.

Cell Substrates—Membranes and Scaffolds

The membrane can be made of a variety of materials that are suitable for cell growth and construct conditioning. The material is ideally biocompatible and sterilizable. The membrane can be made of a permanent or biodegradable/bioresorbable natural or synthetic polymer, can be porous or non-porous, permanent or biodegradable, and can have a variety of pore diameters, from 0.01 micron up to approximately 8 to 10 microns.

Cell growth membranes are well known in the art. Examples of biodegradable materials from which the membrane can be made are poly-$\epsilon$-caprolactone, polyesters, polylactides, polyvinyl alcohols, polyglycolides, polyolefins, and polyanhidrides. Non-biodegradable materials which can be used as a membrane include nitrocellulose, cellulose ester, nylon, polypropylene, polyvinylchloride, and their derivatives. In one embodiment the membrane is a thin (10 micron) semipermeable (0.2 micron) polycarbonate membrane.

A scaffold is a three dimensional framework that allows attachment and growth of cells. A scaffold can be used in the device, in addition to or instead of the membrane, to provide a structure for the cells to grow upon. The scaffold can be made of the same types of materials as recited for the membrane above. Such scaffolds are known in the art.

Size

The size of the bioreactor can vary and will be selected according to the size of the construct to be grown or conditioned. The membrane area or scaffold size will also vary depending upon the size of the construct to be grown or conditioned. Generally, implanted constructs will range from about 1 to 5 mm in diameter and be 1 to 3 mm thick. Multiple punches for implantation can be taken out of one construct if desired. In one embodiment, the flow chamber is 1.8 inches long and 0.5 inches wide and the growth area is 5.8 cm$^2$ (a clinically relevant size for orthopedic implants). The dimensions of the flow chamber, along with flow rate, are variables in the shear stress that can be achieved, as discussed below.

The bioreactor is scaleable so long as the fluid dynamics are kept the same. This would likely require additional ports (and perfusion lines, etc.) if the width was increased. The length can be increased without any significant redesign; however, a decrease in length would alter the fluid dynamics.

II. Assembly and Operation

As further explained below, the bioreactor can be used in both a static mode and a dynamic, or perfusion, mode. Static mode is used for growth of cells or tissue without the influence of mechanical forces. In perfusion mode, the device is capped, creating a defined fluid chamber above the cells or construct, through which media can be pumped, for example using a peristaltic pump and tubing (not shown).

For static growth or conditioning, the cap is not used, instead the bioreactor is topped with the cover 52. After the membrane 28 is selected and fastened to the frame 16, the bottom plate 14, frame 16, and top plate 12 are stacked in order. Screws or other fastening elements (not shown) are used with the fastening holes 24 to fasten the three parts together. After placing the cells in the top chamber (see more below), the cover 52 is placed over the top plate 12. The cover 52 desirably does not seal the top plate 12, it simply provides protection from contaminants.

It can be appreciated from the description that a bottom chamber is defined by the bottom plate 14, the walls of the cut out part 26 of the frame 16, and the membrane 28. A top chamber is defined by the membrane 28, the top plate gasket 22, and cover 52 or cap 18. Gaskets 32 and 22 provide a liquid-tight seal between bottom plate 14 and frame 16 and top plate 12 and frame 16, respectively.

The cells are cultured in the bioreactor for the desired period of time, commonly about 2 to 4 weeks but this can vary. Depending on the original cell density, the cells could be cultured infinitely long. Eventually, they would reach a steady-state and would simply require nutrient replenishment. However, cells are generally not cultured in static cultures longer than about two months. Fresh media can be placed in the top chamber and the same or different media can be placed in the bottom chamber and circulated through the bottom chamber, if desired, using ports 34 and 36. Cells can also be seeded into the bottom chamber if desired. Reseedings can be done, if desired, to build layers of different types of cells, for example.

For perfusion, and application of shear stress, the cover 52 is removed and the cap 18 is fastened to the top plate 12 with the fastening elements as described above with respect to the plates 12, 14 and the frame 16. A shim (not shown in the figures) made of plastic or metal, can be placed between the cap 18 and the top plate 12 if desired.

A peristaltic pump, or other type fluid circulation device, is attached to inlet port 48 and outlet port 50. Media is then pumped through the top chamber. Diffusion grooves 46 allow even distribution of the fluid over the cells or construct. The same or a different media can also be perfused through the bottom chamber, from inlet port 36 through the chamber and out outlet port 36. The application of shear stress is continued for the desired time, which will vary, but can be for 3 to 14 days, for example.

The size of the top chamber can be changed by changing the size of the protrusion 44 or the thickness of the shim or the thickness of gasket 22. The size of the bottom chamber can be varied by changing the thickness of the frame 16 or the gasket 32.

The rate of fluid flow through the device can be varied to control two functions: 1) rate of nutrient delivery and 2) amount of shear stress. The formula for shear stress via perfusion in a parallel-plate flow chamber is governed by the following formula:

$$\tau = 6\mu Q/wh^2$$

where $\tau$ is the shear stress, $\mu$ is the media viscosity, Q is flow rate, w is chamber width and h is height of flow channel. Thus, it can be seen that the desired shear stress can be achieved by varying the flow rate and chamber size (assuming the media viscosity is a constant). A desirable shear stress is generally from about 1 to 100 dynes/cm$^2$, more desirably from about 10-20 dynes/cm$^2$. Since different cells respond very differently to different ranges of shear stress, the amount of stress will be varied depending on the cell type being cultured.

Cells

Any adherent cell type can be grown in the bioreactor; i.e. undifferentiated cell types such as mesenchymal stem cells, or differentiated cell types such as chondrocytes, osteoblasts, fibroblasts across many lineages. In a preferred embodiment, bovine articular chondrocytes are grown from high-density monolayer into a tissue resembling native articular cartilage. Different cells can be seeded in the top and bottom chambers and different cells can be seeded in layers during sequential seedings.

Tissue Constructs

The bioreactor can be used to condition tissue constructs that have just been grown in the bioreactor in static mode. It can also be used to condition tissue-engineered constructs made elsewhere and harvested tissues such as autografts, allografts, or xenografts. For example cryopreserved tissues such as meniscal allografts may be preconditioned within the bioreactor to improve cell viability and synthetic activity prior to implantation. A combination approach may also be taken in which cells are seeded onto cryopreserved tissues to enhance their cellularity prior to implantation. Enhanced cellular function either within or on the surface of cryopreserved tissues may accelerate allograft integration and remodeling following implantation.

Biochemical Stimuli

Biochemical stimuli in the form of soluble growth factors can be used, depending on the cell type. For instance, to encourage chondrogenesis, factors like transforming growth-factor beta (TGF-β), fibroblast growth factor (FGF), insulin-like growth factor (IGF), and ascorbic acid can be used. An osteogenic factor such as dexamethasone, a bone morphogenic protein (BMP), vitamin D, or parathyroid hormone (PTH) can also be used. Other factors can be used based on the appropriateness for the cell type or intended function (growth/expansion versus differentiation).

Biomechanical Stimuli

As discussed above, fluid induced shear stress and direct mechanical stress are biomechanical stimuli that can be applied to cells or constructs to induce certain characteristics in the cells or construct. Flow stimulation may be continuous, periodic, or oscillating. Shear stress may be modulated by varying flow rate or fluid viscosity. Other biomechanical stimuli include fluid-induced and direct-mechanical compressive stress/pressurization. These mechanical signals can be static or cyclic in nature.

The device can be designed to apply direct mechanical compression to the cells or construct by making the cap movable perpendicular to the cells/construct. Direct force can be constant or oscillatory.

A combination of biochemical and biomechanical stimuli may be most desirable.

Scaffold

If a scaffold is used, it could be placed in the top chamber, supported by the membrane, in order to maintain a distinct top and bottom compartment. Also, the scaffold could be placed in (what would be) the bottom compartment without a membrane to allow for a more co-culture/composite construct to be cultured.

EXAMPLE

The example below serves to further illustrate the invention, to provide those of ordinary skill in the art with a complete disclosure and description of how the compounds, compositions, articles, devices, and/or methods claimed herein are made and evaluated, and is not intended to limit the scope of the invention. In the example, unless expressly stated otherwise, amounts and percentages are by weight, temperature is in degrees Celsius or is at ambient temperature, and pressure is at or near atmospheric. The example is not intended to restrict the scope of the invention.

Example 1

Growth of Chondrocytes

This experiment shows that chondrocytes can be cultured in the bioreactor and the resulting construct exhibits an increase in type II collagen and mechanical strength after application of shear stress via perfusion.

The bioreactor had a top chamber 1.8 inches long and 0.5 inches wide; the growth area was 5.8 cm$^2$. The cells were primary 2 to 4 week old bovine articular chondrocytes. The cells were plated at high densities ($2\times10^6$ cells/cm$^2$) in the top chamber of the bioreactor onto a porous, thin (10 micron), semipermeable (0.2 micron) polycarbonate membrane.

The cells were statically cultured for 2 weeks in a DMEM base media, supplemented with 10% fetal bovine serum (FBS), non-essential amino acids, ascorbic acid and gentamycin sulfate, and then subjected to shear stress (about 15 dynes/cm$^2$) for 72 hrs in the bioreactor using perfusion. The flow rate was approximately 20 mL/min.

Results

Histological analysis showed the up-regulation of type II collagen after perfusion, with no substantial change in type I collagen. Type II collagen is the predominant type in cartilage. Histology also showed tissue heterogeneity. The Athrogen-CIA (Chondrex, Inc.) enzyme-linked immunosorbent assay (ELISA) showed a quantitative increase in type II collagen. Mechanical testing showed a functional increase in Young's modulus after perfusion.

Modifications and variations of the present invention will be apparent to those skilled in the art from the forgoing detailed description. All modifications and variations are intended to be encompassed by the following claims. All publications, patents, and patent applications cited herein are hereby incorporated by reference in their entirety.

What is claimed is:

1. A bioreactor for culturing cells or conditioning a tissue construct, comprising:
    a frame to which a cell growth substrate or tissue construct can be attached;
    first and second growth or conditioning chambers on each side of the frame, wherein the chambers are separate when the substrate or construct is attached to the frame;
    a separate fluid supply for each chamber;
    diffusion grooves connected with the fluid supply in the first chamber so that fluid flowing through the fluid supply into the chamber applies shear stress to the cells or tissue in the chamber; and
    inlet and outlet tubes, each having a plurality of diffusion ports along its length, connected to the fluid supply of the second chamber.

2. The bioreactor of claim 1, further comprising a cell growth substrate attached to the frame, wherein the substrate is a membrane or a scaffold to which cells can attach.

3. The bioreactor of claim 1, wherein the bioreactor can be operated in static mode or dynamic mode.

4. The bioreactor of claim 1, having a top chamber defined by a cap, a gasket, and the frame and a bottom chamber defined by a bottom plate, a gasket, and the frame,
    wherein each of the chambers has an inlet and outlet port for fluid flow through the chamber,
    wherein the diffusion grooves are in the top chamber cap and connected with the inlet and outlet ports so that the fluid supply through the chamber applies shear stress to the cells or tissue in the chamber; and
    wherein the cap of the top chamber seals tightly to the gasket and frame so that fluid can be passed through the chamber under pressure.

* * * * *